(12) United States Patent
Klug et al.

(10) Patent No.: US 9,452,121 B2
(45) Date of Patent: Sep. 27, 2016

(54) COMPOSITION CONTAINING AMINO ACID SURFACTANTS, BETAINES AND N-METHYL-N-ACYLGLUCAMINES AND HAVING IMPROVED FOAM QUALITY AND HIGHER VISCOSITY

(71) Applicants: Peter Klug, Grossostheim (DE); Carina Mildner, Frankfurt am Main (DE)

(72) Inventors: Peter Klug, Grossostheim (DE); Carina Mildner, Frankfurt am Main (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 14/401,337

(22) PCT Filed: May 29, 2013

(86) PCT No.: PCT/EP2013/061076
§ 371 (c)(1),
(2) Date: Nov. 14, 2014

(87) PCT Pub. No.: WO2013/178684
PCT Pub. Date: Dec. 5, 2013

(65) Prior Publication Data
US 2015/0141466 A1    May 21, 2015

(30) Foreign Application Priority Data
May 30, 2012 (DE) ................ 10 2012 010 657

(51) Int. Cl.
| | | |
|---|---|---|
| A61K 8/60 | (2006.01) | |
| A61K 8/49 | (2006.01) | |
| A61Q 19/00 | (2006.01) | |
| A61K 8/365 | (2006.01) | |
| A61Q 19/10 | (2006.01) | |
| A61K 8/44 | (2006.01) | |
| A61K 8/34 | (2006.01) | |
| A61Q 5/02 | (2006.01) | |
| A61K 8/42 | (2006.01) | |
| C11D 1/94 | (2006.01) | |
| C11D 3/43 | (2006.01) | |
| C11D 1/52 | (2006.01) | |
| C11D 1/90 | (2006.01) | |
| C11D 1/10 | (2006.01) | |

(52) U.S. Cl.
CPC ............... *A61K 8/60* (2013.01); *A61K 8/345* (2013.01); *A61K 8/365* (2013.01); *A61K 8/42* (2013.01); *A61K 8/44* (2013.01); *A61K 8/442* (2013.01); *A61K 8/4913* (2013.01); *A61K 8/4926* (2013.01); *A61K 8/4973* (2013.01); *A61Q 5/02* (2013.01); *A61Q 19/00* (2013.01); *A61Q 19/10* (2013.01); *C11D 1/94* (2013.01); *C11D 3/43* (2013.01); *A61K 2800/48* (2013.01); *A61K 2800/524* (2013.01); *A61K 2800/596* (2013.01); *C11D 1/10* (2013.01); *C11D 1/525* (2013.01); *C11D 1/90* (2013.01)

(58) Field of Classification Search
None
See application file for complete search history.

(56) References Cited

U.S. PATENT DOCUMENTS

| | | |
|---|---|---|
| 5,194,639 A | 3/1993 | Connor et al. |
| 8,178,481 B2 | 5/2012 | Sans et al. |
| 2013/0216491 A1* | 8/2013 | Ogihara ............. A61K 8/33 424/70.13 |
| 2015/0125415 A1 | 5/2015 | Klug et al. |
| 2015/0126424 A1 | 5/2015 | Klug et al. |
| 2015/0126616 A1 | 5/2015 | Klug et al. |
| 2015/0133560 A1 | 5/2015 | Klug et al. |
| 2015/0140048 A1 | 5/2015 | Klug et al. |
| 2015/0141466 A1 | 5/2015 | Klug et al. |
| 2015/0141508 A1 | 5/2015 | Klug et al. |
| 2015/0150767 A1 | 6/2015 | Klug et al. |
| 2015/0164755 A1 | 6/2015 | Klug et al. |
| 2015/0164756 A1 | 6/2015 | Klug et al. |
| 2016/0074310 A1 | 3/2016 | Klug et al. |

FOREIGN PATENT DOCUMENTS

| | | |
|---|---|---|
| EP | 0 285 786 | 10/1998 |
| WO | 98/56496 | 12/1998 |

OTHER PUBLICATIONS

Quack, et al., Fette—Seifen—Anstrichmittel 78, 200, (1976).
International Search Report for PCT/EP2013/061076, mail date May 15, 2014.

* cited by examiner

*Primary Examiner* — Kristin Vajda
(74) *Attorney, Agent, or Firm* — Tod A. Waldrop

(57) ABSTRACT

The invention relates to a composition which contains at least one N-acyl-amino acid surfactant, a betaine surfactant, an N-methyl-N-acylglucamine, said N-methyl-N-acylglucamine having a $C_{16}$-$C_{20}$-acyl group, and further contains a solvent and optionally one or more additives. The invention also relates to a method for producing the composition. The invention further relates to the use of the composition for the treatment or care of skin or hair, or for use as a shampoo, face cleaner, liquid cleaner or shower gel.

16 Claims, No Drawings

COMPOSITION CONTAINING AMINO ACID SURFACTANTS, BETAINES AND N-METHYL-N-ACYLGLUCAMINES AND HAVING IMPROVED FOAM QUALITY AND HIGHER VISCOSITY

The invention relates to a composition comprising at least one N-acylamino acid surfactant, a betaine surfactant, an N-methyl-N-acylglucamine, a solvent and optionally one or more additives, and to a method for preparing the composition. The invention relates further to the use of the composition for the treatment or care of the skin or hair or as a shampoo, facial cleanser, liquid cleanser or shower gel.

The production of liquid products in the cosmetics and detergents sector is increasing constantly. Especially in the field of body cleansing agents, it is liquid hair shampoos, foam baths and shower gels which have increasingly gained importance in recent years. Liquid dishwashing detergents and mild liquid detergents have likewise won a firm place on the market. It is important to establish an appropriate viscosity for the various applications, which is achieved by the addition of thickeners. Ideally, only small amounts of thickeners or no thickeners at all are necessary.

EP 0 285 786 describes uses of N-polyhydroxyalkyl fatty acid amides as thickeners for liquid aqueous surfactant systems. This object was achieved by the use of N-polyhydroxyalkyl fatty acid amides of formula I

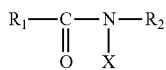

wherein $R_1$ is an optionally branched alkyl radical having from 1 to 17 carbon atoms, preferably from 7 to 17 carbon atoms,
$R_2$ is hydrogen, an optionally branched, optionally unsaturated alkyl radical having from 1 to 18 carbon atoms, preferably from 1 to 6 carbon atoms, or a radical

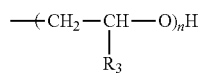

wherein n=0 or from 1 to 5 and $R_3$ can be hydrogen or —$CH_3$, and X represents a polyhydroxyalkyl radical having from 4 to 7 carbon atoms which is optionally glycosidically bonded to a mono-, di- or oligo-saccharide residue, as thickeners for liquid aqueous surfactant systems. However, that patent specification does not describe the thickening of amino acid surfactants and uses as thickener an N-acyl-N-methylglucamine surfactant having an alkyl chain distribution of coconut oil and thus having a small proportion of longer-chained $C_{16}$-$C_{20}$ glucamides.

WO 98/56496 describes a surfactant composition having improved foam stability. The surfactant composition comprises: (a) from approximately 1 to approximately 40% by weight of a sugar-based surfactant; (b) from approximately 1 to approximately 40% by weight of an anionic surfactant; (c) from approximately 0.11 to approximately 10% by weight of an amphoacetate; and (d) remainder water, wherein the amounts by weight are based on the weight of the composition.

A requirement for a good surfactant formulation is good storage stability. The composition must not become cloudy or form sediment in the case of fluctuations in temperature and should have a viscosity which can be adapted to the particular intended use. Accordingly, the viscosity is a quality criterion. The degree of viscosity depends on the surfactant system and the electrolyte addition. It is known that the thickeners known from the prior art do not exhibit a sufficient increase in viscosity in the presence of paraffin sulfonates (see Fette-Seifen-Anstrichmittel 78, 200, (1976)). Amino acid surfactants such as acyl glycinates, acyl aspartates or acyl glutamates, on the other hand, despite being well tolerated by the skin, cannot be thickened sufficiently in many cases and were therefore hitherto not economical as the primary surfactant because of the high. Surprisingly, it has been found that longer-chained, but not shorter-chained, N-acyl-N-methylglucamines are suitable as excellent cosurfactants having a high thickening capacity for compositions comprising amino acid surfactants.

Accordingly, the object of the present invention is to provide improved compositions, in particular with regard to improved viscosity adjustment.

There is accordingly provided a composition comprising:
(A) at least one N-acyl-amino acid surfactant as component A,
(B) at least one betaine surfactant as component B,
(C) at least one N-methyl-N-acylglucamine as component C, wherein the N-methyl-N-acylglucamine has a $C_{16}$-$C_{20}$-acyl radical,
(D) at least one solvent as component D, and
(E) optionally one or more additives as component E.

The composition according to the invention advantageously has an increased viscosity.

Further terms for N-methyl-N-acylglucamine are N-methyl-N-1-deoxysorbitol fatty acid amide, N-acyl-N-methyl-glucamine, glucamide or N-methyl-N-alkylglucamide. N-Methyl-N-acylglucamine corresponds to formula (X), wherein R is an organic radical:

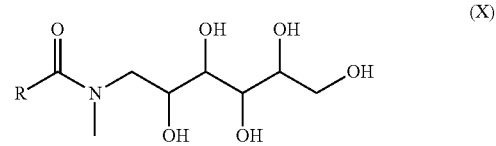

An N-acyl-amino acid surfactant is understood as being, for example, an acylated amino acid.

Within the scope of a preferred embodiment, the composition comprises:
(A) from 5 to 15% by weight of component A,
(B) from 1 to 10% by weight of component B,
(C) from 1 to 10% by weight of component C,
(D) from 10 to 93% by weight of a protic solvent as component D, and
(E) from 0 to 10% by weight of component E,
wherein the sum of components A to E is 100% by weight. Preferably, the composition consists of
(A) from 5 to 15% by weight of component A,
(B) from 1 to 10% by weight of component B,
(C) from 1 to 10% by weight of component C,
(D) from 10 to 93% by weight of a protic solvent as component D, and
(E) from 0 to 10% by weight of component E,
wherein the sum of components A to E is 100% by weight.

Within the scope of a preferred embodiment, the amino acid radical of component A is selected from the group consisting of proteinogenic amino acids, their N-alkylated derivatives or mixtures thereof.

Preference is given as component A to acyl glycinates, acyl alaninates, acyl aspartates, acyl glutamates and acyl sarcosinates, in particular sodium cocoyl glycinate, potassium cocoyl glycinate, sodium lauroyl glycinate, potassium lauroyl glycinate, sodium cocoyl glutamate, sodium lauroyl glutamate, sodium cocoyl aspartate, sodium lauroyl aspartate and sodium lauroyl sarcosinate.

Within the scope of a preferred embodiment, component A consists of at least one $C_8$-$C_{22}$-acylated amino acid, in particular N-alkylated derivatives thereof. Preference is given to the corresponding lauroyl or cocoyl derivatives of the amino acids.

Within the scope of a preferred embodiment, component A is selected from the group consisting of acyl glycinate, acyl aspartate, acyl glutamate, acyl sarcosinate or mixtures thereof.

Within the scope of a preferred embodiment, component B comprises at least one alkyl betaine and/or at least one alkylamido betaine.

Examples of suitable alkyl betaines are the carboxyalkylation products of secondary and in particular tertiary amines of formula (III)

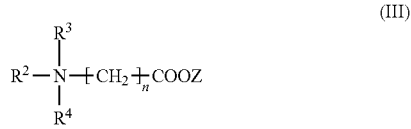

(III)

wherein $R^2$ represents alkyl and/or alkenyl radicals having from 6 to 22 carbon atoms, $R^3$ represents hydrogen or alkyl radicals having from 1 to 4 carbon atoms, $R^4$ represents hydrogen or alkyl radicals having from 1 to 4 carbon atoms, n represents numbers from 1 to 6, and Z represents an alkali and/or alkaline earth metal or ammonium. Typical examples are the carboxymethylation products of hexylmethylamine, hexyldimethylamine, octyldimethylamine, decyldimethylamine, dodecylmethylamine, dodecyl-dimethylamine, dodecylethylmethylamine, C12/14-coco alkyldimethyl-amine, myristyldimethylamine, cetyldimethylamine, stearyldimethylamine, stearylethylmethylamine, oleyldimethylamine, C16/18-tallow alkyldimethyl-amine, and commercial mixtures thereof.

Examples of suitable alkylamoid betaines are carboxyalkylation products of amidoamines. Particularly suitable are amidopropyl betaines of formula (IV)

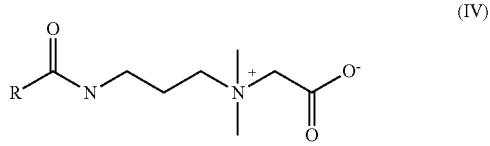

(IV)

wherein $R^5$ is a linear or branched saturated $C_7$-$C_{21}$-alkyl group or a linear or branched mono- or poly-unsaturated $C_7$-$C_{21}$-alkenyl group.

Preferred betaine surfactants are amidopropyl betaines such as cocoamidopropyl betaine ($R^5CO$ is the fatty acid radical of coconut oil, chain length $C_8$-$C_{18}$) and alkyl betaines such as coco-betaine ($R^2$ is the alkyl radical of coconut oil, chain length $C_8$-$C_{18}$) or lauryl betaine ($R^2$ is an alkyl radical of chain length $C_{12}$ and $C_{14}$).

Within the scope of a preferred embodiment, component C consists of a mixture of N-methyl-N-acylglucamines, wherein at least 80% by weight of the N-methyl-N-acylglucamines have a saturated or unsaturated $C_{16}$- or $C_{18}$-acyl radical. For example, N-methyl-N-acylglucamines which have a $C_{14}$-acyl radical but wherein at least 80% by weight of the N-methyl-N-acylglucamines have a saturated or unsaturated $C_{16}$- or $C_{18}$-acyl radical may also be present in the mixture. Component C preferably consists of a mixture of N-methyl-N-acylglucamines wherein at least 90% by weight of the N-methyl-N-acylglucamines have a saturated or unsaturated $C_{16}$- or $C_{18}$-acyl radical.

A solvent within the scope of the present invention is preferably understood as being protic solvents such as water, $C_1$-$C_8$-alcohols, in particular $C_1$-$C_6$-alcohols, ethylene glycol, diethylene glycol, triethylene glycol or mixtures thereof, particular preference being given to water and/or ethanol or water and/or methanol. Of the $C_1$-$C_6$-alcohols, methanol, ethanol, isopropanol, n-butanol or sec-butanol are preferred.

Within the scope of a preferred embodiment, the solvent of component D is water or a mixture of water and propylene glycol.

Within the scope of a preferred embodiment, the composition is free of alkyl sulfates and/or alkyl ether sulfates. Free means that the composition contains less than 3% by weight, based on the total amount of the composition, preferably less than 0.5% by weight and in particular no alkyl sulfates and/or alkyl ether sulfates.

Within the scope of a preferred embodiment, the sum of components A, B and C is from 7 to 20% by weight, preferably from 8 to 18% by weight, and in particular from 10 to 15% by weight.

Within the scope of a preferred embodiment, the additives are selected from the group consisting of preservatives, fragrances, dyes, further surfactants, water, oily substances, cationic polymers, film-forming agents, thickeners and gelling agents, superfatting agents, antimicrobial and biogenic active ingredients, moisture-donating substances, stabilizers, acids, lyes, activity enhancers and mixtures thereof, preferably in amounts of from 0.1 to 10.0% by weight, particularly preferably from 0.5 to 8.0% by weight, and in particular from 1.0 to 5.0% by weight.

Suitable preservatives are preservatives listed in the relevant annex to the European cosmetic products legislation, for example phenoxyethanol, benzyl alcohol, parabens, benzoic acid and sorbic acid; particularly suitable are, for example, 1,3-bis(hydroxymethyl)-5,5-dimethylimidazolidine-2,4-dione (Nipaguard® DMDMH), piroctone olamine, methylisothiazolinone or mixtures thereof, preferably piroctone olamine and/or methylisothiazolinone.

As fragrances or perfumes or oils there can be used individual fragrance compounds, for example synthetic products of the ester, ether, aldehyde, ketone, alcohol and hydrocarbon type. Examples of fragrance compounds of the ester type are benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, linear alkanals having from 8 to 18 carbon atoms, citral, citronellal, citronellyloxy acetaldehyde, cyclamen aldehyde, hydroxycitronellal, lilial and bourgeonal; the ketones include, for example, ionones, alpha-isomethylionone and methyl cedryl ketone; the alcohols include anethol, citronellol, eugenol, geranion, linalool, phenylethyl alcohol and terpineol; the hydrocarbons include mainly terpenes and balsams. Preference is given to the use of mixtures of different fragrances, which together produce a pleasant note.

Perfume oils can also comprise natural fragrance mixtures, as are obtainable from plant or animal sources, for example pine oil, citrus oil, jasmine oil, lily oil, rose oil or ylang-ylang oil. Ethereal oils of low volatility, which are mostly used as flavor components, are also suitable as perfume oils, for example salvia oil, chamomile oil, carnation oil, melissa oil, mint oil, cinnamon leaf oil, linden blossom oil, juniper berry oil, vetiver oil, olibanum oil, galbanum oil and ladanum oil.

The desired viscosity of the compositions can be adjusted (increased or lowered) by adding thickeners and gelling agents. There come into consideration preferably cellulose ethers and other cellulose derivatives (for example carboxymethylcellulose, hydroxyethylcellulose), gelatin, starch and starch derivatives, sodium alginates, fatty acid polyethylene glycol esters, agar-agar, tragacanth or dextrin derivatives, in particular dextrin esters. Also suitable are metal salts of fatty acids, preferably having from 12 to 22 carbon atoms, for example sodium stearate, sodium palmitate, sodium laurate, sodium arachidate, sodium behenate, potassium stearate, potassium palmitate, sodium myristate, aluminum monostearate, hydroxy fatty acids, for example 12-hydroxystearic acid, 16-hydroxyhexadecanoic acid; fatty acid amides; fatty acid alkanolamides; dibenzalsorbitol and alcohol-soluble polyamides and polyacrylamides or mixtures thereof. There can further be used crosslinked and uncrosslinked polyacrylates such as carbomers, sodium polyacrylates or sulfonic-acid-containing polymers such as ammonium acryloyldimethyltaurate/VP copolymer.

There are used as antimicrobial active ingredients cetyltrimethylammonium chloride, cetylpyridinium chloride, benzethonium chloride, diisobutylethoxy-ethyldimethylbenzylammonium chloride, sodium N-lauryl sarcosinate, sodium N-palmethyl sarcosinate, lauroyl sarcosine, N-myristoylglycine, potassium N-lauryl sarcosine, trimethylammonium chloride, sodium aluminum chlorohydroxylactate, triethyl citrate, tricetylmethylammonium chloride, 2,4,4'-trichloro-2'-hydroxydiphenyl ether (triclosan), phenoxyethanol, 1,5-pentanediol, 1,6-hexanediol, 3,4,4'-trichlorocarbanilide (triclocarban), diaminoalkylamide, for example L-lysine hexadecylamide, citrate heavy metal salts, salicylates, piroctose, in particular zinc salts, pyrithiones and heavy metal salts thereof, in particular zinc pyrithione, zinc phenolsulfate, farnesol, ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, selenium disulfide and octopirox, iodopropynyl butylcarbamate, methyl-chloroisothiazolinone, methylisothiazolinone, methyldibromo glutaronitrile, AgCl, chloroxylenol, sodium salt of diethylhexyl sulfosuccinate, sodium benzoate, as well as phenoxyethanol, benzyl alcohol, phenoxyisopropanol, parabens, preferably butyl-, ethyl-, methyl- and propyl-paraben, and sodium salts thereof, pentanediol, 1,2-octanediol, 2-bromo-2-nitropropane-1,3-diol, ethylhexylglycerol, benzyl alcohol, sorbic acid, benzoic acid, lactic acid, imidazolidinylurea, diazolidinylurea, dimethyloldimethylhydantoin (DMDMH), sodium salt of hydroxymethyl glycinate, hydroxyethylglycine of sorbic acid, and combinations of these active substances.

The compositions according to the invention can further comprise biogenic active ingredients selected from plant extracts, such as, for example, aloe vera, as well as local anesthetics, antibiotics, antiphlogistics, antiallergics, corticosteroids, sebostatic agents, Bisabolol®, Allantoin®, Phytantriol®, proteins, vitamins selected from niacin, biotin, vitamin B2, vitamin B3, vitamin B6, vitamin B3 derivatives (salts, acids, esters, amides, alcohols), vitamin C and vitamin C derivatives (salts, acids, esters, amides, alcohols), preferably as the sodium salt of the monophosphoric acid ester of ascorbic acid or as the magnesium salt of the phosphoric acid ester of ascorbic acid, tocopherol and tocopherol acetate, as well as vitamin E and/or derivatives thereof.

There can be used as stabilizers metal salts of fatty acids, such as, for example, magnesium stearate, aluminum stearate and/or zinc stearate.

There are available as the moisture-donating substance, for example, isopropyl palmitate, glycerol and/or sorbitol. Sorbitol is particularly preferred.

The compositions according to the invention can further comprise film-forming agents, which are selected, according to the intended use, from salts of phenylbenzimidazolesulfonic acid, water-soluble polyurethanes, for example $C_{10}$-polycarbamyl polyglyceryl ester, polyvinyl alcohol, polyvinylpyrrolidone copolymers such as PVP/hexanedecene or PVP/eicosene copolymer, for example vinylpyrrolidone/vinyl acetate copolymer, water-soluble acrylic acid polymers/copolymers or esters or salts thereof, for example partial ester copolymers of acrylic/methacrylic acid and polyethylene glycol ethers of fatty alcohols, such as acrylate/steareth-20 methacrylate copolymer, water-soluble cellulose, for example hydroxymethylcellulose, hydroxyethylcellulose, hydroxypropyl-cellulose, water-soluble quaterniums, polyquaterniums, carboxyvinyl polymers, such as carbomers and salts thereof, polysaccharides, for example polydextrose and glucan, vinyl acetate/crotonate, for example obtainable under the trade name Aristoflex® A 60 (Clariant), as well as polymeric amine oxides, for example representatives obtainable under the trade names Diaformer Z-711, 712, 731, 751.

There can be used as superfatting agents preferably lanolin and lecithin, non-ethoxylated and polyethoxylated or acylated lanolin and lecithin derivatives, polyol fatty acid esters, mono-, di- and tri-glycerides and/or fatty acid alkanolamides, the latter at the same time acting as foam stabilizers.

As acids or lyes for adjusting the pH there are preferably used mineral acids, in particular HCl, inorganic bases, in particular NaOH or KOH, or organic acids, in particular lactic acid.

Sorbitan caprylate can preferably be used as the activity enhancer.

Within the scope of a preferred embodiment, the composition is a cosmetic, dermatological or pharmaceutical composition.

The invention further provides a method for preparing the composition according to the invention, comprising the steps:

a) mixing component E with D to form a solution,
b) adding component A to the solution from a),
c) mixing component D with optionally a further component E, preferably a humectant, and then adding the mixture to the solution from step b),
d) adding components B and C, in particular in succession, to the solution from c), and
e) adjusting the composition to a pH of from 6.8 to 7.5.

In a further variant, the composition according to the invention is prepared using (A) from 5 to 15% by weight of component A,
(B) from 1 to 10% by weight of component B, (C) from 1 to 10% by weight of component C,
(D) from 10 to 93% by weight of a protic solvent as component D, and
(E) from 0 to 10% by weight of component E,
wherein the sum of components A to E is 100% by weight.

The invention further provides the use of the composition according to the invention as a shampoo, facial cleanser, liquid cleanser or shower gel.

The invention further provides the use of the composition according to the invention for the treatment or care of the skin.

The invention further provides the use of the composition according to the invention for the treatment or care of the hair.

The invention will be explained in greater detail by the following examples.

PREPARATION EXAMPLES P1 AND P2, EXAMPLE 1 AND COMPARATIVE EXAMPLES 1 AND 2

The N-acyl-N-methyl-glucamines described in the following were prepared according to EP 0 550 637 from the corresponding fatty acid methyl esters and N-methylglucamine in the presence of 1,2-propylene glycol as solvent and were obtained in the form of a solid consisting of active substance and 1,2-propylene glycol.

TABLE 1

| Preparation Example | Methyl ester | Active substance (%) | 1,2-Propylene glycol (%) | Melting point |
|---|---|---|---|---|
| P1 | C12/14 | 90 | 10 | 85 |
| P2 | C16/18 | 80 | 20 | 68 |
| P3 | C16/18' | 80 | 20 | 50 |

C12/14 means that the methyl ester consists of a mixture of lauric acid methyl ester ($C_{12}$-acyl radical) and myristic acid methyl ester ($C_{14}$-acyl radical) (ratio 75:25). C16/18 means that the methyl ester consists of a mixture of palmitic acid methyl ester ($C_{16}$-acyl radical) and stearic acid methyl ester ($C_{18}$-acyl radical) (ratio 30:70). C16/18' means that the methyl ester consists of a mixture of palmitic acid methyl ester, stearic acid methyl ester, oleic acid methyl ester and linoleic acid methyl ester (ratio 30:10:50:10).

The viscosities are measured at 20 revolutions/minute and 20° C. using a Brookfield viscometer model DV II, the spindles from the RV spindle set. Spindles 1 to 7 from the RV spindle set are used. Under these measuring conditions, spindle 1 is chosen for viscosities of not more than 500 mPa·s, spindle 2 for viscosities of not more than 1000 mPa·s, spindle 3 for viscosities of not more than 5000 mPa·s, spindle 4 for viscosities of not more than 10,000 mPa·s, spindle 5 for viscosities of not more than 20,000 mPa·s, spindle 6 for viscosities of not more than 50,000 mPa·s and spindle 7 for viscosities of not more than 200,000 mPa·s.

In the following test formulation, the N-acyl-methylglucamine according to Preparation Examples P2 and P3 was tested in comparison with Preparation Example P1 and in comparison with alkyl polyglucosides.

Preparation Procedure
I Mixing of components E (Octopirox® (Clariant)) and D (water).
II Addition of component A to I and subsequent stirring until the solution is clear.
III Mixing of components D (water) and E (sorbitol) and subsequent stirring until the solution is clear.
IV Addition of III to II and homogenization.
V Addition in succession of components B (Genagen® KB (Clariant)), C (sugar-based surfactant) and E (Velsan® SC(Clariant)) to IV and subsequent stirring until the solution is clear.
VI Adjustment of the pH by means of component E (lactic acid) to a value of from 7.0 to 7.2.
VII Addition of component E (SkyBio® M500) to VII, homogenization.

The composition and preparation are summarized in Table 2.

TABLE 2

Gentle hair shampoo

| Step | Component | Name | Property | |
|---|---|---|---|---|
| I | E | Octopirox ® (Clariant) Piroctone olamine | Preservative | 0.10% |
|  | D | Water | Solvent | 10.00% |
| II | A | Hostapon SG ® (Clariant) (25% solution in water, calculated on active content) Sodium cocyl glycinate | Surfactant | 7.50% |
| III | D | Water | Solvent | to 100% |
|  | E | Sorbitol | Humectant | 1.00% |
| IV | B | Genagen ® KB (Clariant) (30% solution in water, calculated on active content) Coco-betaine | Co-surfactant | 4.50% |
|  | C | Sugar-based surfactant | Co-surfactant | 4.80% |
|  | E | Velsan ® SC (Clariant) Sorbitan caprylate | Activity enhancer | 1.00% |
| V | E | Lactic acid, 25% | Neutralizer | to pH = 7 |
| VI | E | SkyBio ® M500 Methylisothiazolinone | Preservative | 0.02% |

TABLE 3

| Example | Sugar-based surfactant | Viscosity at 20° C. (mPas) |
|---|---|---|
| Example 1 | Preparation Example P2 | 27900 |
| Example 2 | Preparation Example P3 | 9500 |
| Comparative Example 1 | Preparation Example P1 | 1710 |
| Comparative Example 2 | Plantacare 818 (coco-glucoside) | 3500 |

The amount of sugar-based surfactant used of 4.8% is based on the active content of the surfactant, that is to say the amount of coco-glucoside (Plantacare 818/BASF SE) used corresponds to 9.23% as the commercial product. The N-acyl-N-methylglucamines were used on the basis of the active content from Table 1.

As is apparent from Examples 1 and 2, C16/18 N-acyl-N-methylglucamines exhibit an excellent thickening capacity both compared with shorter-chained N-acyl-N-methylglucamines (Comparative Example 1) and compared with alkyl polyglucosides (Comparative Example 2).

Moreover, the formulations have a stable viscosity even at low temperatures.

The invention claimed is:
1. A composition comprising:
(A) at least one N-acylamino acid surfactant as component A,
(B) at least one betaine surfactant as component B,

(C) at least one N-methyl-N-acylglucamine as component C, wherein the N-methyl-N-acylglucamine has a $C_{16}$-$C_{20}$-acyl radical, (D) at least one solvent as component D, and (E) optionally one or more additives as component E.

2. The composition as claimed in claim 1, comprising:

(A) from 5 to 15% by weight of component A, (B) from 1 to 10% by weight of component B, (C) from 1 to 10% by weight of component C, (D) from 10 to 93% by weight of a protic solvent as component D, and (E) from 0 to 10% by weight of component E, wherein the sum of components A to E is 100% by weight.

3. The composition as claimed in claim 1, wherein the amino acid radical of component A is selected from the group consisting of proteinogenic amino acids, their N-alkylated derivatives and mixtures thereof.

4. The composition as claimed in claim 1, wherein component A consists of at least one $C_8$-$C_{22}$-acylated amino acid.

5. The composition as claimed in claim 1, wherein component A is selected from the group consisting of acyl glycinate, acyl aspartate, acyl glutamate, acyl sarcosinate and mixtures thereof.

6. The composition as claimed in claim 1, wherein component B comprises at least one alkyl betaine and/or at least one alkylamido betaine.

7. The composition as claimed in claim 1, wherein component C consists of a mixture of N-methyl-N-acylglucamines, wherein at least 80% by weight of the N-methyl-N-acylglucamines have a saturated or unsaturated $C_{16}$- or $C_{18}$-acyl radical.

8. The composition as claimed in claim 1, wherein the solvent of component D is water or a mixture of water and propylene glycol.

9. The composition as claimed in claim 1, wherein the composition is free of alkyl sulfates and/or alkyl ether sulfates.

10. The composition as claimed in claim 1, wherein the sum of components A, B and C is from 7 to 20% by weight.

11. The composition as claimed in claim 1, wherein the one or more additives are selected from the group consisting of preservatives, fragrances, dyes, further surfactants, water, oily substances, cationic polymers, film-forming agents, thickeners and gelling agents, superfatting agents, antimicrobial and biogenic active ingredients, moisture-donating agents, stabilizers, acids, lyes, activity enhancers, and mixtures thereof.

12. The composition as claimed in claim 1, wherein the composition is a cosmetic, dermatological or pharmaceutical composition.

13. A method for preparing the composition as claimed in claim 1, comprising the steps:

a) mixing component E with D to form a solution, b) adding component A to the solution from step a), c) mixing component D with optionally a further component E and then adding to the solution from step b) to form a solution, d) adding components B and C to the solution from step c), and e) adjusting the pH of the composition to a range of 6.8 to 7.5.

14. A shampoo, facial cleanser, liquid cleanser or shower gel comprising a composition as claimed in claim 1.

15. A skin treatment or skin care product comprising a composition as claimed in claim 1.

16. A hair treatment or hair care product comprising a composition as claimed in claim 1.

\* \* \* \* \*